(12) United States Patent
Van Wees

(10) Patent No.: US 9,150,470 B2
(45) Date of Patent: Oct. 6, 2015

(54) PROCESS FOR CONTACTING ONE OR MORE CONTAMINATED HYDROCARBONS

(75) Inventor: Mark Van Wees, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 918 days.

(21) Appl. No.: 13/365,210

(22) Filed: Feb. 2, 2012

(65) Prior Publication Data

US 2013/0204062 A1 Aug. 8, 2013

(51) Int. Cl.
| | | |
|---|---|---|
| C07C 1/00 | (2006.01) |
| C07C 7/00 | (2006.01) |
| C10G 45/02 | (2006.01) |
| C10G 45/22 | (2006.01) |

(52) U.S. Cl.
CPC . *C07C 7/00* (2013.01); *C10G 45/02* (2013.01); *C10G 45/22* (2013.01); *C10G 2300/1077* (2013.01)

(58) Field of Classification Search
CPC ............ C10G 1/02; C10G 1/04; C10G 1/042; C10G 7/003; C10G 7/006; C10G 7/06; B01D 1/065; B01D 1/26; B01D 3/06; B01D 3/14; B01D 11/0284
USPC .................. 208/177; 585/240; 196/14.52, 128
See application file for complete search history.

(56) References Cited

U.S. PATENT DOCUMENTS

| | | | |
|---|---|---|---|
| 1,582,123 A | 4/1926 | Clark |
| 2,896,261 A | 7/1959 | McAfee |
| 3,085,522 A | 4/1963 | Quintin |
| 3,316,958 A | 5/1967 | Johnston |
| 3,428,106 A | 2/1969 | Johnston |
| 3,449,220 A | 6/1969 | Geisler et al. |
| 3,865,574 A | 2/1975 | Long et al. |
| 4,039,429 A | 8/1977 | Van Klinken et al. |
| 4,073,719 A | 2/1978 | Whisman et al. |
| 4,160,692 A | 7/1979 | Mitchell et al. |
| 4,173,246 A | 11/1979 | Nunlist et al. |
| 4,342,645 A | 8/1982 | Fletcher et al. |
| 4,360,420 A | 11/1982 | Fletcher et al. |
| 4,549,904 A | 10/1985 | Matsumiya et al. |
| 4,601,813 A | 7/1986 | Izumi et al. |
| 4,655,903 A | 4/1987 | Rahbe et al. |
| 4,663,022 A | 5/1987 | Gomi et al. |
| 4,673,486 A | 6/1987 | Orihashi et al. |
| RE32,792 E | 11/1988 | Izumi et al. |
| 5,259,947 A | 11/1993 | Kalback et al. |
| 5,273,623 A | 12/1993 | Granelli |

(Continued)

FOREIGN PATENT DOCUMENTS

| | | |
|---|---|---|
| CN | 101104832 A | 1/2008 |
| WO | 8704455 | 7/1987 |

OTHER PUBLICATIONS

Bishop et al., "Evaporators: Use in Re-Refining", Hydrocarbon Processing, Jul. 1979, vol. 58, No. 7, pp. 131-136.

(Continued)

*Primary Examiner* — Nina Bhat
(74) *Attorney, Agent, or Firm* — James C. Paschall

(57) ABSTRACT

One exemplary embodiment can be a process. The process can include contacting one or more contaminated hydrocarbons with a hydrogen gas stream in a flash feed separator to generate a first liquid stream, stripping the first liquid stream to generate a residue stream, and separating the residue stream in a film generating evaporator to obtain a recovered distillate.

20 Claims, 1 Drawing Sheet

(56) References Cited

U.S. PATENT DOCUMENTS

| | | |
|---|---|---|
| 5,312,543 A | 5/1994 | Taylor et al. |
| 5,320,741 A | 6/1994 | Johnson et al. |
| 5,328,596 A * | 7/1994 | Gammie, II .................. 208/321 |
| 5,374,348 A | 12/1994 | Sears et al. |
| 5,538,621 A | 7/1996 | Kalback et al. |
| 5,916,826 A | 6/1999 | White |
| 5,980,732 A | 11/1999 | Gillis |
| 6,001,162 A | 12/1999 | Hayner et al. |
| 6,048,448 A | 4/2000 | Nirell |
| 6,060,631 A * | 5/2000 | James et al. .................. 585/241 |
| 6,103,101 A | 8/2000 | Fragelli et al. |
| 6,170,286 B1 | 1/2001 | Keuper |
| 6,297,353 B1 | 10/2001 | Fuenzalida Diaz et al. |
| 6,331,245 B1 | 12/2001 | Moretta et al. |
| 6,361,682 B1 | 3/2002 | Moretta et al. |
| 6,660,157 B2 | 12/2003 | Que et al. |
| 7,384,540 B2 | 6/2008 | Galeazzi |
| 7,638,040 B2 * | 12/2009 | Van Wees et al. ............. 208/177 |
| 2003/0047486 A1 | 3/2003 | Cash et al. |
| 2004/0232045 A1 | 11/2004 | Simmons et al. |
| 2006/0000703 A1 | 1/2006 | Mason et al. |
| 2006/0006101 A1 | 1/2006 | Eppig et al. |
| 2006/0102007 A1 | 5/2006 | Martin |
| 2006/0118466 A1 | 6/2006 | Galeazzi et al. |
| 2007/0034550 A1 | 2/2007 | Hedrick et al. |
| 2007/0108098 A1 | 5/2007 | Flint et al. |
| 2007/0144944 A1 | 6/2007 | Del Bianco et al. |
| 2007/0232846 A1 | 10/2007 | Baumgartner et al. |
| 2007/0278088 A1 | 12/2007 | Musial |
| 2008/0210600 A1 | 9/2008 | O'Connor et al. |
| 2008/0230440 A1 | 9/2008 | Graham et al. |
| 2008/0230442 A1 | 9/2008 | Iqbal et al. |
| 2008/0289999 A1 | 11/2008 | Lenglet |
| 2009/0000985 A1 | 1/2009 | Van Wees et al. |
| 2009/0048465 A1 | 2/2009 | Feng et al. |
| 2009/0166254 A1 | 7/2009 | Subramanian et al. |
| 2009/0223862 A1 * | 9/2009 | MacDonald .................. 208/184 |
| 2010/0243423 A1 | 9/2010 | Ogawa et al. |
| 2010/0326887 A1 | 12/2010 | McGehee et al. |
| 2010/0329935 A1 | 12/2010 | McGehee et al. |
| 2012/0088702 A1 * | 4/2012 | Zink et al. .................... 508/111 |

OTHER PUBLICATIONS

"Thin Film Evaporators & Short Path Evaporators" "GIG Karasek brochure", Not Later Than Oct. 11, 2011, p. 12 pages.

Kinetics Technology Group, Inc., "KTI Launches Used Oil Recycling Push with N. Calif. Plant", Oil & Gas Journal, Nov. 3, 1986, vol. 84, No. 44, p. 35.

"Lube Oil Reclamation—Acid Free Process", Hydrocarbon Asia, Oct. 1997, vol. 7, No. 7, p. 33.

Magnabosco et al., "Mohawk—CEP Re-Refining Process Produces High Quality Lube Base Oils", 213th ACS National Meeting; ACS Division of Petroleum Chemistry, Inc. Preprints, Feb. 1997, vol. 42, No. 1, pp. 204-207.

* cited by examiner

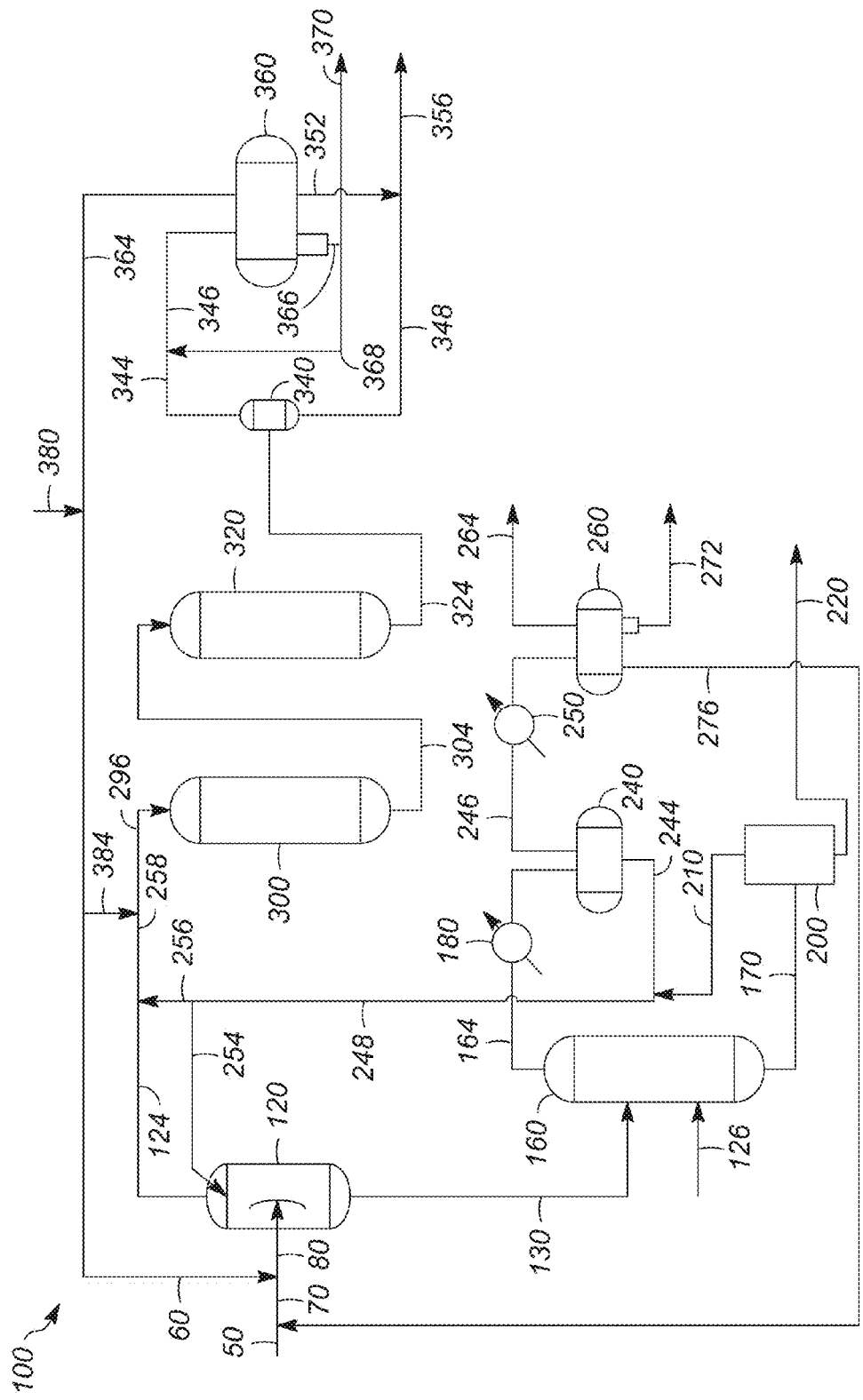

PROCESS FOR CONTACTING ONE OR MORE CONTAMINATED HYDROCARBONS

FIELD OF THE INVENTION

The present invention generally relates to a process for contacting one or more contaminated hydrocarbons.

DESCRIPTION OF THE RELATED ART

Generally, renewable sources of hydrocarbons are increasing in importance. With renewable resources, the dependence on imported oil for petroleum based products can be reduced and a substitute for imported oil may be provided. Often, used petroleum based products, such as waste lubricating oils, or oil derived from carbonaceous waste are recycled and reprocessed. Typically, there is a tremendous amount of oil that is discarded each year, and reprocessing, or re-refining, can recover a substantial amount of product from spent lubricants and other carbonaceous waste materials. Moreover, recovery and reprocessing of contaminated hydrocarbons can also reduce that amount of material requiring environmentally safe disposal.

However, there is a desire to improve recovery and reprocessing to produce higher valued products.

SUMMARY OF THE INVENTION

One exemplary embodiment can be a process. The process can include contacting one or more contaminated hydrocarbons with a hydrogen gas stream in a flash feed separator to generate a first liquid stream, stripping the first liquid stream to generate a residue stream, and separating the residue stream in a film generating evaporator to obtain a recovered distillate.

Another exemplary embodiment may be a process. The process may include contacting one or more contaminated hydrocarbons with a hydrogen gas stream in a flash feed separator to generate a first liquid stream comprising one or more $C22^+$ hydrocarbons, stripping the first liquid stream to generate a residue stream comprising one or more $C28^+$ hydrocarbons, and separating the residue stream in a wiped film evaporator to obtain a recovered distillate comprising one or more C22-C35 hydrocarbons.

A further exemplary embodiment can be a process. The process may include contacting one or more contaminated hydrocarbons with a hydrogen gas stream in a flash feed separator to generate a first liquid stream, stripping the first liquid stream to generate a residue stream, separating the residue stream in a film generating evaporator to obtain a recovered distillate, passing the recovered distillate to a hydroprocessing reactor to obtain a hydroprocessing effluent stream, and separating the hydroprocessing effluent stream to obtain a lubricating oil.

The embodiments disclosed herein can further process a residue product by utilizing a film generating evaporator to produce a recovered distillate. The recovered distillate can be further processed to obtain a lubricating oil product stream.

DEFINITIONS

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three carbon atoms and/or more.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 50%, and preferably about 70%, by mole, of a compound or class of compounds in a stream.

As used herein, the term "substantially" can mean an amount of at least generally about 80%, preferably about 90%, and optimally about 99%, by mole, of a compound or class of compounds in a stream.

As used herein, the term "hydroprocessing" can refer to a process utilizing hydrogen to treat one or more hydrocarbons. Hydroprocessing can include hydrocracking, hydrodemetallization, hydrotreating, hydrodewaxing, hydroisomerization, and/or aromatic hydrotreating. As an example, hydrocracking can refer to a process that hydrocarbons can crack in the presence of hydrogen and optionally catalyst to lower molecular weight hydrocarbons. As a further example, hydrotreating can refer to a process that removes heteroatoms, such as sulfur, nitrogen, and metals from a hydrocarbon feedstock by contacting hydrocarbons with hydrogen in the presence of a suitable catalyst. Hydrotreating can also saturate hydrocarbons with double and triple bonds as well as aromatics. Aromatic hydrotreating may also be specifically designed to saturate aromatics.

As depicted, process flow lines in the figures can be referred to interchangeably as, e.g., lines, pipes, feeds, distillates, condensates, remainders, mixtures, portions, hydrocarbons, effluents, products, or streams.

As used herein, the term "fluid" can mean one or more gases, one or more liquids, and/or one or more vapors.

As used herein, the term "gas" can mean a single gas or a solution of a plurality of gases.

As used herein, the term "liquid" can mean a single liquid, or a solution or a suspension of one or more liquids with one or more gases and/or solid particles.

As used herein, the term "vapor" can mean a gas or a dispersion that may include or consist of one or more hydrocarbons. A dispersion may include one or more of a gas, a liquid, and a solid, such as a dispersion of an aerosol and/or a fog.

As used herein, the term "non-distillable component" can include finely divided particulate matter that can tend to foul hot heat exchange surfaces, form coke on catalyst, deactivate catalyst, and/or plug catalyst beds. Generally, the finely divided particulate matter can include polymerized organic matter.

As used herein, a boiling point may be determined by ASTM Method D2887-97, unless another method is specified.

BRIEF DESCRIPTION OF THE DRAWING

The FIGURE is a schematic depiction of an exemplary re-refining zone.

DETAILED DESCRIPTION

Referring to the FIGURE, an exemplary re-refining zone 100 can include a flash feed separator 120, a stripper 160, a film generating evaporator 200, a hot separator 240, a cold separator 260, a first hydroprocessing reactor 300, a second hydroprocessing reactor 320, a separator 340, and a further separator 360. An exemplary process for upgrading hydrocarbons is disclosed in, e.g., U.S. Pat. No. 7,638,040.

One or more contaminated hydrocarbons can be provided as a stream 50 to the re-refining zone 100. The stream 50 may contain a sufficient amount of non-distillable components that may be adverse to catalyst and equipment used in processing hydrocarbons. The stream 50 may contain no more than about 50%, about 30%, or even about 25%, by weight, one or more non-distillable components. Usually, the one or more contaminated hydrocarbons can include at least one of a carbonaceous waste stream, a petroleum product, and a pyrolysis oil. Additionally, the one or more contaminated hydrocarbons can include one or more of a slurry oil, a vacuum bottoms, a visbroken vacuum residue, a vacuum residue, a heavy vacuum gas oil, a deasphalted bottom material, an off-specification asphalt, an oil storage tank sediment, an atmospheric residuum, a spent solvent from a solvent recovery unit, a used dielectric fluid, a black liquor, a tall oil, a vegetable oil, a waste grease, a tallow oil, and an oil derived from an animal fat. Often, an atmospheric residuum boils at least about 340° C., and a vacuum residue boils at least about 420° C., or even at least about 510° C. The boiling points can be calculated by procedures in appendix A7 of ASTM D1160-06.

Generally, the stream 50 is contacted with a hydrogen gas stream 60, typically rich in hydrogen gas, to at least partially form a feed stream 80 prior to entering a flash feed separator 120. The hydrogen gas stream 60 may be maintained at a temperature higher than the stream 50. Preferably, the hydrogen gas stream 60 can be at a temperature of about 260-about 650° C. A portion of the one or more contaminated hydrocarbons may vaporize in the flash feed separator 120 and generate a first vapor stream 124 and a first liquid stream 130. The first liquid stream 130 may include one or more $C22^+$ hydrocarbons, and may have a boiling point of at least about 371° C. The hydrogen gas stream 60 may serve as a heat source used to directly heat the stream 50 to preclude the coke formation, a diluent to reduce the partial pressure of the feed during vaporization in the flash zone, a possible reactant to minimize the formation of polymers at elevated temperatures, a stripping medium, and at least a portion of the hydrogen required in the hydroprocessing reactors 300 and 320.

The first vapor stream 124 can include hydrogen from the hydrogen gas stream 60 and one or more hydrocarbons vaporized from the stream 50. Generally, the hot contact conditions in the flash feed separator 120 are such that adverse reactions such as thermal degradation can occur. Therefore, preferably the liquid residence time in the flash feed separator 120 is chosen to achieve the maximization of the vaporization of the hydrocarbons with the minimization of adverse thermal reactions. The residence time can vary based upon the temperatures required to vaporize the hydrocarbons from the stream 50.

Under certain circumstances, the feed stream 80 can include a high percentage of non-distillable components and additional liquid can be utilized to wash the non-distillable components from the flash feed separator 120. A vapor wash oil or flush liquid might be an oil having a high boiling point range and including one or more $C22^+$ hydrocarbons, preferably one or more $C30^+$ hydrocarbons, such as a heavy vacuum gas oil, an atmosphere resid, or a vacuum tower bottoms stream, which can have a boiling point of at least about 368° C., or preferably at least about 448° C. The selection of a flush liquid may depend upon the composition of the stream 50 and the prevailing flash conditions in the flash feed separator 120, and the volume of the flush liquid is preferably limited to that required for removal of the heavy non-distillable component.

Generally, the first liquid stream 130 can contain residual distillable hydrocarbons that have not been vaporized and be withdrawn from the flash feed separator 120. The first liquid stream 130 may be provided to a stripper 160, without intermediate heating or cooling, where a hot gas stream 126 may be used to strip the first liquid stream 130 and generate a second vapor stream 164 including one or more vaporized hydrocarbons and at least a portion of the hot gas stream 126. Preferably, the flash feed separator 120 minimizes the amount of distillable components in the first liquid stream 130 to no more than about 80%, preferably no more than about 40%, by weight. In a preferred operation, the stripper 160 is a vacuum stripper, and the stripping gas is super-heated steam. However, other stripping gases including hydrogen may also be utilized. A residue stream 170 from the stripper 160 can include non-distillable components, such as solids and other impurities, and one or more $C28^+$ hydrocarbons, which may have a boiling point of at least about 431° C.

The residue stream 170 can be provided to a film generating evaporator 200. The film generating evaporator 200 may include a thin film evaporator, a wiped film evaporator, a falling film evaporator, a rising film evaporator, or a scraped surface evaporator. Preferably, the film generating evaporator is a wiped film evaporator. Other film generating evaporators may also be used, such as a stripping evaporator, a horizontal-tube evaporator, a calandria-type evaporator, a short path evaporator, a long-tube vertical evaporator, and a forced circulation evaporator.

A film generating evaporator 200 can promote evaporation of at least a portion of the residue stream 170 sufficiently quickly to avoid coking. Often, a film generating evaporator includes a moving part for renewing the surface with a portion of the residue stream 170. Exemplary film generating evaporators are disclosed in, e.g., U.S. Pat. Nos. 3,316,958; 4,160, 692; and 4,173,246.

A thin film evaporator (may be abbreviated herein as "TFE") may heat the residue stream 170 on an internal surface of a heated tube until the residue begins to evaporate. The residue can be maintained as a thin film on the internal surface of the tube by a rotating blade with a fixed clearance. The vapors are then liquefied on the cooler tubes of a condenser.

A wiped film evaporator (may be abbreviated herein as "WFE") is typically different from a TFE in that it uses a hinged blade with minimal clearance from the internal surface to agitate the flowing residue to effect separation. In both TFE and WFE, the residue can enter the unit tangentially above a heated internal tube and may be distributed evenly over an inner circumference of the tube by the rotating blade. The residue can spiral down the wall while bow waves developed by rotor blades may generate highly turbulent flow and optimum heat flux. The residue may evaporate rapidly and vapors can flow either co-currently or counter-currently against the residue. In some exemplary TFE and WFE designs, the residue may be condensed in a condenser located outside but as close to the evaporator as possible. As an example, a short path distillation unit can include a TFE or a WFE that has an internal condenser.

In a falling film evaporator (may be abbreviated herein as "FFE"), the residue can enter the evaporator at the head and may be evenly distributed into heating tubes. Generally, a thin film enters the heating tubes and flows downward at boiling temperature and is partially evaporated. An inert gas, such as steam, may be used for heating the tubes by contact with the outside of the tubes. The residue can flow downward in the tubes into a lower separator in which the vaporous hydrocarbons may be separated from heavier hydrocarbons.

Generally, a rising film evaporator (may be abbreviated herein as "RFE") operates on a thermo-siphon principle. The residue can enter a bottom of heating tubes heated by steam provided on the outside of the tubes. As the residue heats, vapor begins to form and ascend. The ascending force of this vapor can cause liquid and vapors to flow upward in parallel flow. At the same time, the production of vapor increases and the liquid may be pressed as a thin film on the walls of the tubes while ascending. Usually, the co-current upward movement against gravity has the beneficial effect of creating a high degree of turbulence in the residue that can promote heat transfer and coke inhibition.

A scraped surface evaporator (may be abbreviated herein as "SSE") can operate similarly as a WFE. However, an SSE typically endeavors to keep a film of pitch on the heated surface from overheating by frequent removal with a scraper rather than maintain a thin film on the internal heated surface.

Usually, the film generating evaporator 200 can produce a recovered distillate 210 and a residue product 220. The recovered distillate 210 may include one or more C22-C35 hydrocarbons and boil at about 370- about 480° C. The residue product 220 can include non-distillable components such as solids and other impurities and may be sold as asphalt blending components or as a supplemental fuel in a cement kiln or steel mill, passed to storage, or routed to other units for further processing. The residue product 220 can include one or more C28+ hydrocarbons, and may have a boiling point of at least about 426° C. The recovered distillate 210 can be combined with a recovered oil stream 244, as hereinafter described, for the recovery of, e.g., lubricating oil products. The recovered oil stream 244 can include one or more C18-C25 hydrocarbons and may have a boiling point of about 315-about 400° C.

Typically, the second vapor stream 164 is a hot hydrocarbon gas stream that is condensed in a first condenser 180 to liquefy the hydrocarbons recovered in the stripper 160 and passed to a hot separator 240. Often, the condensed liquid is separated into the recovered oil stream 244 and the uncondensed vapor is a third vapor stream 246.

Preferably, the hot separator 240 is operated at a temperature above the dew point of the hot gas stream 126. The third vapor stream 246 can be condensed in a second condenser 250 and provided to the cold separator 260. Various streams can be provided from the cold separator 260, namely a gas stream 264, a condensate stream 272, and the recycled oil stream 276. The gas stream 264 can be utilized as, e.g., fuel gas, or further processed. The condensate stream 272 may be disposed or further processed as well. The recycled oil stream 276 can be combined with the stream 50 to form a combined feed stream 70 prior to receiving the hydrogen gas stream 60.

Generally, the recovered oil stream 244 is combined with the recovered distillate 210 and at least a remainder 256 from this combined stream 248 is passed to be merged with the first vapor stream 124 to form a combined stream 258. A portion 254 of the combined stream 248 can be provided to the flash feed separator 120 as a flush stream 254, which can be distributed via one or more sprayers or through packing or trays.

The combined stream 258 can receive a split hydrogen stream 384 from the hydrogen rich vapor stream 364, as hereinafter described, to form a feed stream 296. The feed stream 296 can include hydrogen and hydrocarbons. Usually, the feed stream 296 is passed to the first hydroprocessing reactor 300. In this exemplary embodiment, the first hydroprocessing reactor 300 can be a hydrodemetallization reactor 300, although any suitable hydroprocessing reactor may be used, such as a hydrocracking reactor or a hydrotreating reactor. The hydrodemetallization reactor 300 can contain a hydrodemetallization catalyst for contacting the feed stream 296 at hydrodemetallization conditions, and generate a hydrodemetallization effluent stream 304. The hydrodemetallization catalyst also reacts with the hot hydrocarbonaceous vapor to remove sulfur compounds, to perform some denitrification, to hydrodeoxygenate the oil and to remove some heteroatoms in addition to metals from the oil. Generally, the hydrodemetallization reactor 300 operates at a temperature of about 150-about 450° C. and a pressure of about 0.100-about 14 MPa. The hydrodemetallization reactor 300 may contain a fixed, fluidized, or ebullated catalyst bed. The recovered distillate 210 and the recovered oil stream 244 may aid in controlling temperatures of the first vapor stream 124 by cooling the first vapor stream 124 before passing to the hydrodemetallization reactor 300.

Often, the hydrodemetallization effluent stream 304 is passed to the second hydroprocessing reactor 320 for contacting with a hydroprocessing catalyst to increase the hydrogen content in the hydrocarbons. The hydroprocessing to a greater extent may react the hot hydrocarbonaceous vapor to remove sulfur compounds, to perform deep denitrification and hydrodeoxygenation of the hydrocarbons and to saturate aromatic compounds. The processing conditions are also at a temperature and under sufficient hydrogen partial pressure that some cracking of the larger hydrocarbon molecules will occur. The processing conditions and catalyst for hydroprocessing are similar to the hydrodemetallization reactor 300. Generally, the second hydroprocessing reactor 320 operates at a temperature of about 200-about 450° C., and a pressure of about 0.100-about 14 MPa. The second hydroprocessing reactor 320 may contain a fixed, fluidized, or ebullated catalyst bed, and is operated at hydroprocessing conditions to produce a hydroprocessing effluent stream 324 including hydroprocessed hydrocarbons. The hydroprocessing effluent stream 324 may be cooled with, e.g., a cooler, to generate a liquid-vapor stream provided to a separator 340.

Usually, a vapor stream 344 including hydrogen, gaseous water soluble inorganic compounds, and lower boiling hydrocarbons, and a liquid stream 348 including one or more hydrocarbons are recovered from the separator 340. The liquid stream 348 may include recovered liquid hydrocarbons for use as a lubricating oil product stream or other commercially valuable liquids. Thus, liquid stream 348, which may optionally be further processed, can include a lubricating oil.

The vapor stream 344 may be cooled and contacted with an aqueous scrubbing solution provided by a recycle stream 368 to remove acidic gases for recycling hydrogen gases contained therein, and the resulting mixture 346 can be sent to the further separator 360. The aqueous scrubbing solution preferably includes a basic compound such as sodium carbonate or ammonium hydroxide. The aqueous solution neutralizes and dissolves water soluble inorganic compounds. The contact with an aqueous scrubbing solution can be performed in any convenient manner, including in-line mixing, which may be promoted by a means for mixing. The aqueous scrubbing solution is preferably introduced in an amount of about 1-about 100%, by volume, based on the hydroprocessing effluent stream 324 from the second hydroprocessing reactor 320. The vapor stream 344 and the recycle stream 368 may be combined as the resulting mixture 346 passed to the further separator 360 for removal of some liquid carryover.

The further separator 360 can provide a liquid stream 352, such as a lubricating oil product stream 352, a hydrogen rich vapor stream 364, and an aqueous stream 366. The liquid stream 352 can be combined with the liquid stream 348 to form a combined stream 356, which can be a lubricating oil product stream 356.

The hydrogen rich vapor stream 364 may be scrubbed prior to recycling and combining with additional hydrogen from a make-up stream 380 to provide the hydrogen for the split hydrogen stream 384 and hydrogen gas stream 60. The hydrogen rich vapor stream 364 may be no less than about 70%, preferably no less than about 85%, by volume, hydrogen. After combining with the make-up stream 380 of hydrogen and removing the split hydrogen stream 384, the hydrogen gas stream 60 is heated with, e.g., an exchanger, and recycled to contact with the combined feed stream 70 to form the feed stream 80 in the flash feed separator 120.

The aqueous stream 366 can be obtained from a boot of the further separator 360 and be split into the recycle stream 368 that is contacted with the vapor stream 344 and a purge stream 370 that may be sent to any suitable destination for treating and/or disposing. Although not shown, a make-up stream of the aqueous scrubbing solution may be added to the recycle stream 368 to correspond to the amount of the purge stream 370.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process, comprising:
   A) contacting one or more contaminated hydrocarbons with a hydrogen gas stream in a flash feed separator to generate a first liquid stream;
   B) stripping the first liquid stream to generate a residue stream; and
   C) separating the residue stream in a film generating evaporator to obtain a recovered distillate.

2. The process according to claim 1, wherein the film generating evaporator comprises a thin film evaporator, a wiped film evaporator, a falling film evaporator, a rising film evaporator, or a scraped surface evaporator.

3. The process according to claim 1, wherein the film generating evaporator comprises a wiped film evaporator.

4. The process according to claim 1, wherein the one or more contaminated hydrocarbons comprises at least one of a carbonaceous waste stream, a petroleum product, and a pyrolysis oil.

5. The process according to claim 1, wherein the one or more contaminated hydrocarbons comprises a petroleum product, which in turn comprises one or more of a slurry oil, an atmospheric residuum, a spent solvent from a solvent recovery unit, a used dielectric fluid, a black liquor, a tall oil, a vegetable oil, a waste grease, a tallow oil, and an oil derived from an animal fat.

6. The process according to claim 1, wherein the first liquid stream comprises one or more $C22^+$ hydrocarbons.

7. The process according to claim 1, wherein the hydrogen gas stream is at a temperature of about 260-about 650° C.

8. The process according to claim 1, wherein the residue stream comprises one or more $C28^+$ hydrocarbons.

9. The process according to claim 1, wherein the recovered distillate comprises one or more C22-C35 hydrocarbons and boils at about 370-about 480° C.

10. The process according to claim 1, further comprising recovering a residue product from the film generating evaporator.

11. The process according to claim 1, further comprising passing the recovered distillate to a hydrodemetallization reactor.

12. The process according to claim 11, wherein the hydrodemetallization reactor operates at a temperature of about 150-about 450° C., and a pressure of about 0.100-about 14 MPa.

13. A process, comprising:
   A) contacting one or more contaminated hydrocarbons with a hydrogen gas stream in a flash feed separator to generate a first liquid stream comprising one or more $C22^+$ hydrocarbons;
   B) stripping the first liquid stream to generate a residue stream comprising one or more $C28^+$ hydrocarbons; and
   C) separating the residue stream in a wiped film evaporator to obtain a recovered distillate comprising one or more C22-C35 hydrocarbons.

14. A process, comprising:
   A) contacting one or more contaminated hydrocarbons with a hydrogen gas stream in a flash feed separator to generate a first liquid stream;
   B) stripping the first liquid stream to generate a residue stream;
   C) separating the residue stream in a film generating evaporator to obtain a recovered distillate;
   D) passing the recovered distillate to a hydroprocessing reactor to obtain a hydroprocessing effluent stream; and
   E) separating the hydroprocessing effluent stream to obtain a lubricating oil.

15. The process according to claim 14, wherein the film generating evaporator comprises a wiped film evaporator.

16. The process according to claim 14, wherein the hydroprocessing reactor comprises a hydrodemetallization reactor.

17. The process according to claim 14, wherein the hydroprocessing reactor operates at a temperature of about 200-about 450° C., and a pressure of about 0.100-about 14 MPa.

18. The process according to claim 14, wherein the first liquid stream comprises one or more $C22^+$ hydrocarbons.

19. The process according to claim 14, wherein the recovered distillate comprises one or more C22-C35 hydrocarbons.

20. The process according to claim 14, wherein the residue stream comprises one or more $C28^+$ hydrocarbons.

* * * * *